(12) United States Patent  (10) Patent No.: US 6,203,157 B1
Lee  (45) Date of Patent: Mar. 20, 2001

(54) METHOD FOR TESTING VISUAL FUNCTION CAPABLE OF GUARANTEEING VALIDITY THEREOF

(75) Inventor: Keung Hae Lee, Kyoungki-do (KR)

(73) Assignees: Tai Won Lee; Damool Systec Co., Ltd., both of Seoul (KR)

( * ) Notice: Subject to any disclaimer, the term of this patent is extended or adjusted under 35 U.S.C. 154(b) by 0 days.

(21) Appl. No.: 09/356,316

(22) Filed: Jul. 16, 1999

(30) Foreign Application Priority Data

Jul. 16, 1998 (KR) ................................................ 98 -28967

(51) Int. Cl.$^7$ ....................................................... A61B 3/02

(52) U.S. Cl. .............................................................. 351/242

(58) Field of Search .................................... 351/239, 240, 351/241, 242, 243, 211, 221

(56) References Cited

U.S. PATENT DOCUMENTS 4,526,452 * 7/1985 Hirsch .................................. 351/243

* cited by examiner

*Primary Examiner*—George Manuel
(74) *Attorney, Agent, or Firm*—Oblon, Spivak, McClelland, Maier & Neustadt, P.C.

(57) ABSTRACT

Disclosed is a method for testing a visual function (visual acuity and color function) using a display device; and, more particularly, a method for improving accuracy of the visual function testing and reducing human resources in testing the visual function of an examinee. The present invention improves subjective errors caused by the subjective visual function testing and may be easily used in a visual function testing requiring an objective and exact testing results in such as military affairs, vocational aptitude test, driving license, insurance against loss, observation of an ophthalmic ailment. Further, automatic testing method of the present invention is widely used in hospitals, opticians, schools, companies, public health centers, other organization and households where it is difficult to take professional advice with a low cost.

33 Claims, 8 Drawing Sheets

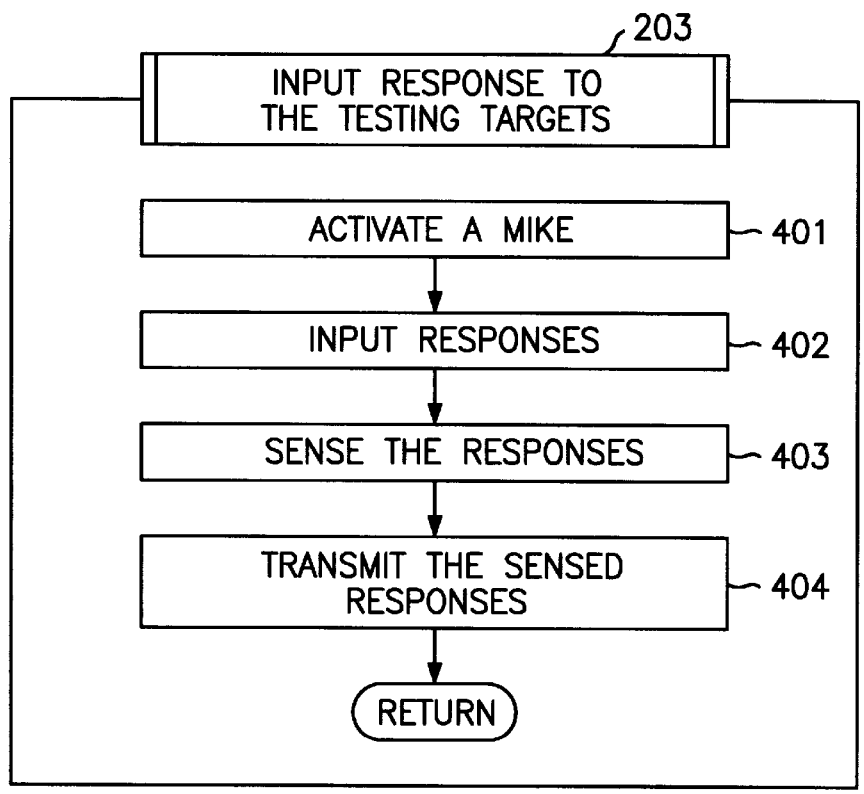
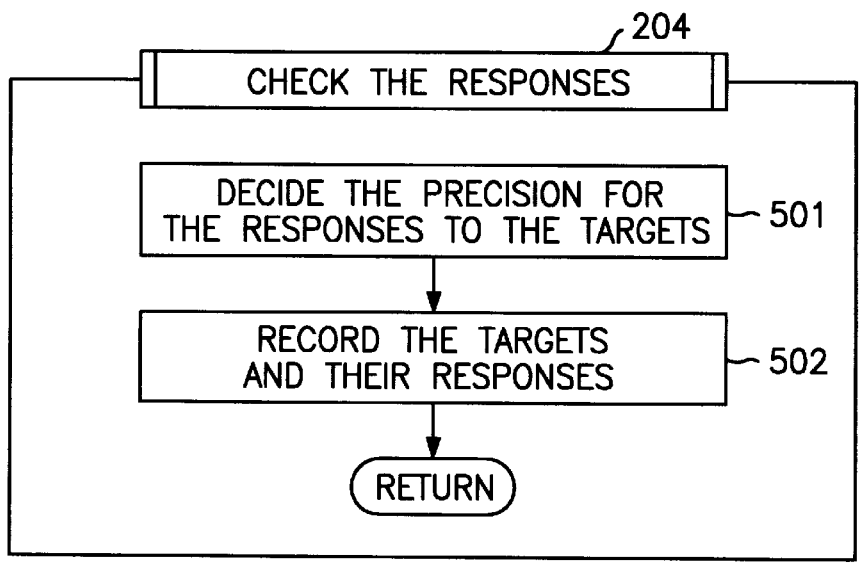

METHOD FOR TESTING VISUAL FUNCTION CAPABLE OF GUARANTEEING VALIDITY THEREOF

FIELD OF THE INVENTION

The present invention relates to a method for testing a visual function (visual acuity and color function) using a display device; and, more particularly, to a method for improving accuracy of the visual function testing and reducing human resources in testing the visual function of an examinee.

DESCRIPTION OF THE PRIOR ARTS

Generally, the conventional visual acuity testing has used the printed visual acuity testing targets (hereinafter, referred to as eyesight testing targets) whose contents are fixed to different targets, such as number, characters and marks. However, in the case where an examinee bears them in mind, the results of the testing can not be reliable. Also, the visual acuity testing using a display device, which shows test patterns in such a manner as to provide only the printed eyesight testing targets, can not prevent the examinee from intentionally feigning his visual function.

Further, the conventional visual acuity testing has the examinee distinguish the eyesight testing targets in duplicate, which are classified by about 10 degrees up to 0.1 from 1.0, and then, the corresponding degree is considered as the examinee's visual acuity. Therefore, the tested visual acuity may not coincide with the examiner's actual degree and it is merely decided in the closest degree of the eyesight testing targets, thereby not precisely measuring the visual acuity.

Such a subjective visual acuity testing as above has a high probability to commit errors in the test result and a problem requiring extra manpower (e.g. nurse(s), doctor(s)) at the time of group test in hospital or school.

Meanwhile, in the conventional color function testing using color targets of "Ishihara" and "Cheon-Seok Han," the examinee can memorize the color function discriminating targets (hereinafter, referred to as color-testing targets) in advance because the number of color targets is relatively small.

Further, "Han's color-testing targets" available for measuring the abnormality of an normal person in the color function testing makes it possible to measure his color function by just three degrees such as fine, medium and poor and "F-M 100-Hue" methods by which the abnormality degree can be more precisely measured should be carried out for a long time to decide the color function, thereby being inconvenient to practically use.

A method for measuring the abnormality degree by use of "Anomaloscope" requires peculiar high price of equipment and, in another method using color-testing targets printed on paper or "F-M 100-Hue" method measuring the degree by indicating the discriminating targets by hand, there is a problem that the colors of targets may be changed after passing a long time and thus, it is difficult to obtain precise result for the abnormality due to the changed colors of the targets.

SUMMARY OF THE INVENTION

It is, therefore, an object of the present invention to provide a visual function testing method for easily performing the testing, heightening the precision of the testing by displaying the discrimination targets on a screen and deciding the examinee's vision function after evaluating the validity by the inputted data of the discriminated response from an examinee.

It is another object of the present invention to provide a visual function testing method for more precisely measuring a visual acuity by randomly producing the size, kinds, contrast, etc. of discrimination targets on a screen; taking the probability of subjective errors down by determining the invalidity of the test result and performing an automatic test based on examinee's discrimination response into a voice recognizing apparatus of the test device; producing visual-testing targets having predetermined size within the resolution range which the screen allows; and deciding the valid visual acuity by detecting the smallest size of the produced visual-testing targets.

It is further object of the present invention to provide a visual function testing method for more precisely measuring the color function testing by randomly producing the color-testing targets on a screen; preventing a feint of the test result by using the randomly produced color-testing targets; improving the probability of subjective errors of the test result; and providing the various degrees of difficulty within some ranges in displaying different hues or contrasts of color to be discriminated.

It is another object of the present invention to provide a visual function testing method for measuring precise result even by only several tests, by applying to the binary search for many discrimination targets necessary for precise measurement of the visual acuity testing or the color function testing.

According to an aspect of the present invention, there is provided a method for testing a visual function of an examinee using a computer system, the method comprising the steps of: a) selecting at least one target to be discriminated; b) producing the selected target on a screen of the computer system; c) inputting a response to the selected target from the examinee; d) ascertaining whether the response is right or wrong; e) repeatedly carrying out the steps of a) to d) in various degrees, comparing the responses to the repeatedly different targets and evaluating a validity of the visual function testing; and f) deciding the visual function of the examinee based on the evaluated validity.

According to another aspect of the present invention, there is provided a method for testing a color function of an examinee using a computer system, the method comprising the steps of: i) displaying at least one color-testing target which is differently discriminated by a normal person and protanope; ii) deciding the examinee to be a protanope if the examinee gives a response to the target, which is discriminated by a protanope; and iii) checking a degree of red blindness by using at least two targets having a different amount of a red component.

According to still another aspect of the present invention, there is provided a method for testing a visual function of an examinee using a computer system, the method comprising the steps of: 1) displaying on a screen a middle value target in a testing range from a lower limited value to a upper limited value; 2) inputting a response to the middle value target from the examinee; 3) ascertaining whether the response is right or wrong; and 4) deciding the examinee's visual acuity, comprising the steps of: 4-1) if the response is wrong, changing the upper limited value based on the middle value target and repeatedly carrying out the steps of 1) to 3); and 4-2) if the response is right, changing the lower limited value based on the middle value target and repeatedly carrying out the steps of 1) to 3).

BRIEF DESCRIPTION OF THE DRAWINGS

The above and other objects and features of the present invention will become apparent from the following description of preferred embodiments given in conjunction with the accompanying drawings, in which:

FIG. 4 is a detailed flow chart illustrating a method for inputting visual-testing response according to this invention;

FIG. 5 is a detailed flow chart for visual-testing response according to the invention;

DETAILED DESCRIPTION OF THE PREFERRED EMBODIMENTS

Hereinafter, the present invention will be described in detail referring to the accompanying drawings.

Figure 1:
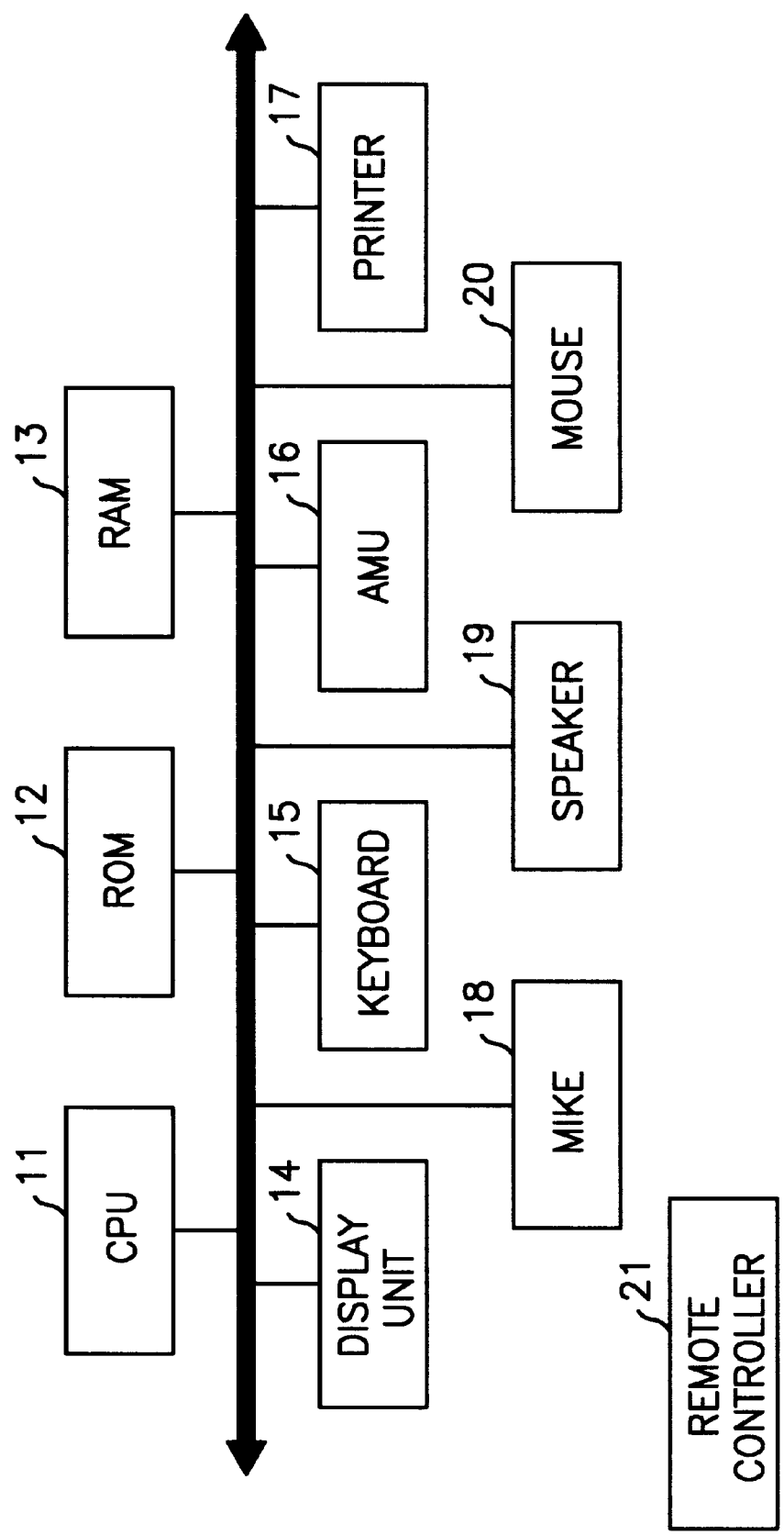
FIG. 1 is a block diagram I illustrating the hardware environment of a visual acuity testing system according to the present invention.

First, referring to FIG. 1, the hardware environment of a visual acuity testing system, to which the present invention is applied, may use a typical computer system including a CPU 11, a ROM 12, a RAM 13, an auxiliary memory unit (AMU) 16, a display unit 14, a keyboard 15, a mike 18, a mouse 20 and a speaker 19. In addition, the hardware environment further includes input devices, such as a remote controller 21 and a printer 17.

However, the hardware environment can be modified and changed, which is well known to those skilled in the art to which the subject matter pertains. Therefore, the present invention will describe a control program loaded on the ROM 12 and/or the RAM 13.

The control program, which is stored in the ROM 12 or the auxiliary memory unit 16, is loaded on the RAM 13 when power is applied to the computer system 10 and then displays the eyesight testing targets on the display unit 14 displays. The responses from the examinee are inputted by an input device such as the mike 18.

Subsequently, a voice recognizing control program stored in the RAM 13 or the ROM 12 recognizes the response from the examinee, evaluates the accuracy of the response and transfers to the RAM 13 data relative to the accuracy. The CPU 11 determines the visual acuity of the examinee using data stored in the RAM 13 and outputs the result of visual acuity to the RAM 13, the auxiliary memory unit (AMU) 16, the display unit 14, the printer 17 and the speaker 19.

On the other hand, when the response from the examinee is inputted via the keyboard 15 or the remote controller 21, the CPU 11 determines the accuracy of the response from the examinee in response to instructions from the control program stored in the RAM 13, determines his visual acuity and outputs the results of the test to the above-mentioned output devices.

Figure 2:
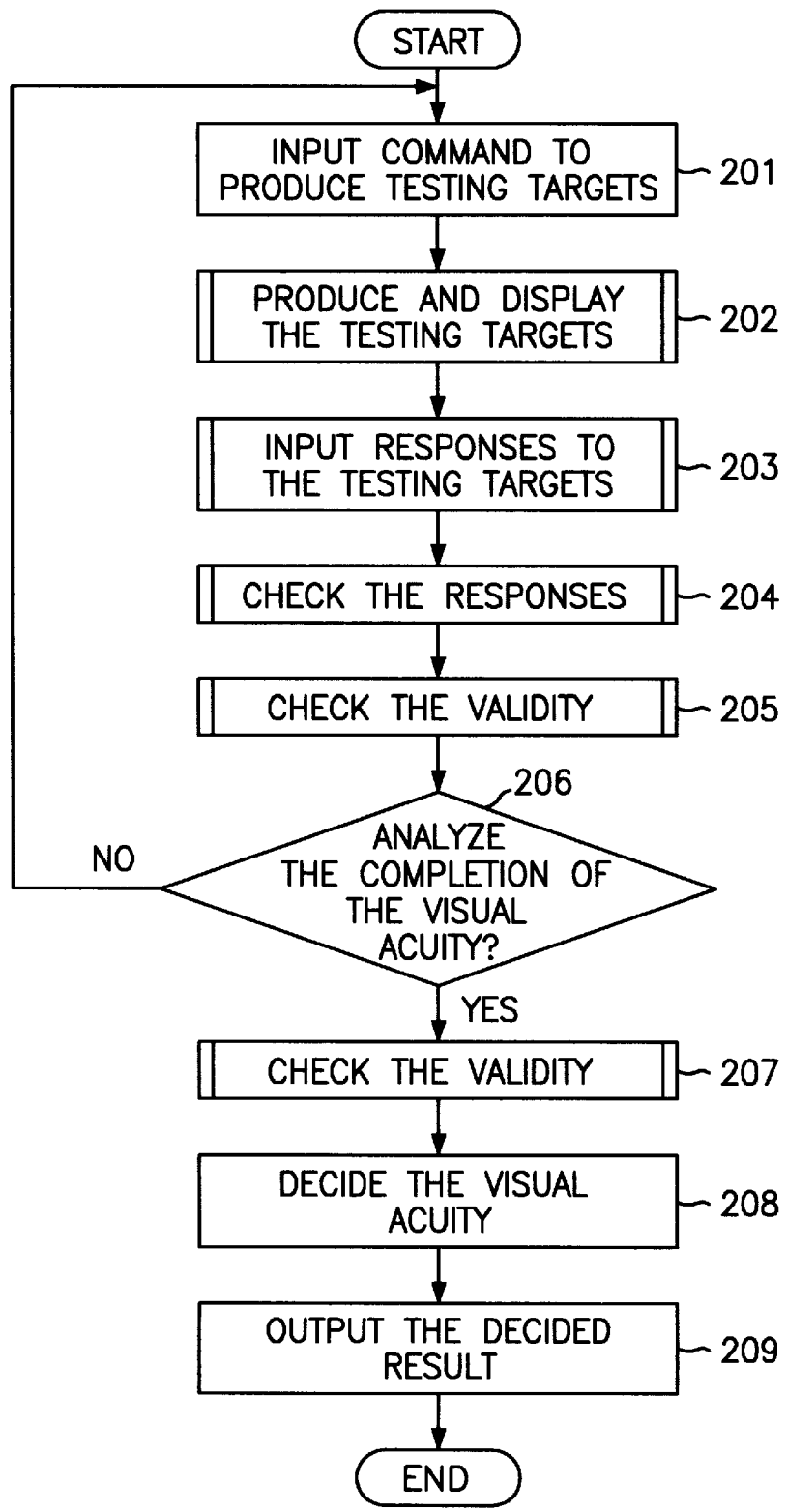
FIG. 2 is a flow chart illustrating a method for testing the visual acuity according to the present invention.

FIG. 2 is a flow chart illustrating a method for testing the visual acuity according to the present invention. This test of the visual acuity is carried out by the control program stored in the ROM 12 and/or the RAM 13.

The computer system (FIG. 1) for the visual acuity testing produces the targets on the display unit 14 (at step 201). In the case of visual acuity testing, the targets are selected from those for testing the visual acuity and, in the case of color function testing, they are selected from images. Accordingly, these targets may be designed for the examinee to simply respond to the shape thereof For example, Ishihara' color-testing target to which numbers are issued as responses, Han's color-testing targets or H-R-R color-testing targets to which simple figures, such as "O" and "X," are issued as responses may be used in the color function testing of the present invention. Also, it is possible to modify the conventional targets or to make new targets. The new targets, for example, targets capable of discriminating the number of red balls can be used in a picture having red and green balls.

Furthermore, the computer system for the visual acuity testing can select and produce the targets for itself and an examiner can command the creation of the targets or select one of them (at step 201) in order that the computer system can display the targets (at step 202).

When the targets are created on the display unit, the examinee may reply to the shape of the targets and the responses from the examinee may be inputted into the computer system by himself or the examiner (at step 203) via various input devices, such as a voice recognizing unit, a keyboard, a wireless remote controller, a mouse and so on.

When the responses from the examinee are inputted into the computer system (at step 203), the computer system checks the response from the examinee (at step 204) and ascertains whether the responses are in accord with the displayed targets.

Next, the computer system analyzes the completion of the visual acuity testing (at step 206). Furthermore, an additional step 205 for checking the validity of the responses may be included after step 204.

For example, in the case of visual acuity testing, if an examinee inputs a right response to a smaller target but he inputs a wrong response to a larger one, the computer system considers the results of visual acuity testing as invalid. So, the above-mentioned validity checking step may be carried out to improve precision in the testing, by performing additional visual acuity testing in the targets to which the examinee gives wrong responses. This additional checking step is achieved by modifying the inner environments of the computer system.

According to the result of the analysis at step 206, if the check for visual acuity testing has not been completed, steps 201 to 205 are repeatedly performed for other targets. If completed, at step 207, it is ascertained whether there is anything that arouses suspicion of the validity in verifying the validity of responses from the examinee.

Step 206, which ascertains whether the visual acuity testing is ready to start or completed, can be determined by different factors based on examiner's selection of testing methods, examinees, environments and time limitation. For example, the completion of the visual acuity testing of the examinee may be made after the visual acuity testing are repeatedly carried out up to the predetermined number of times or it may not be made until the examinee can distinguish the targets which become more and more enlarged. Since this completion of visual acuity decision may be differently made according to the user's requests, the visual acuity testing apparatus according to the present invention may have various selection modes to satisfy the user's requests. For example, the completion of visual acuity testing is made after: 1) the predetermined number of testing is terminated; or 2) wrong responses are repeated several times. That is, the examiner determines the highest degree of the visual acuity, which the examinee can distinguish, and performs the additional visual acuity testing for some targets in the same degree in order to guarantee the accuracy thereof Furthermore, it may be possible for the examinee himself to input a control signal for creating the visual acuity target into the control signal input device at step 201. It should be noted that the completion of visual acuity testing can be determined by various selection of the user.

At step 207, the validity for the results of the visual acuity testing is checked. If the results are considered as valid, the decision is made at step 208 and, if not, the examination is carried out once more or the decision is made with such an invalid notification.

The decision of the visual function at step 208 will be described in detail.

In the case of the visual acuity testing, after testing five (5) targets in the highest degree which the examinee can discriminate, if the examinee discriminates more than three of them, he may be considered as a person who has such a degree. If not, he may be considered as a person who has a just lower degree. Of course, the number of targets and the decision of degree can be changed according to the desired accuracy.

On the other hand, in the case of color function testing, the targets may be selected from one of color charts, which are used in the Ishihara and Han's color-testing targets or HR-R color testing. By using these color targets, a color-blindness test is carried out. Further, in the present invention, new color targets similar to the conventional color targets can be used through the combination of colors, thereby easily testing the color-blindness.

Hereinafter, a red blind person is referred to as a "protanomalous" or "protanope", a green blind a "deuteranomalous" or "deuteranope" and a blue blind a "tritanomalous" or "tritanope."

If there is a response, which is often caused by a protanope, a deuteranope or a tritanope, the present invention examines a color blindness for each color. In the color function testing according to the present invention, the color targets are randomly selected from the color targets, which are stored in a memory. Alternatively, the color targets can be randomly created during the color function testing.

Finally, the visual acuity is decided at step 208 and the decided results are output at step 209. The decided results may be output by various output devices such as monitor, printer and speaker.

The input of the response from the examinee is implemented by various input means such as keyboards, keypads, mousses, remote controllers, joysticks and voice recognizing devices. Also, the responses from the examinee can be input by the examiner or some others. In the preferred embodiment of the present invention, the voice recognition technique may have characteristics of the speaker/independent technique and the isolation word recognition technique for predetermined vocabularies and these techniques have been widely used in the various fields of industry.

For example, there are many products and various techniques, which have high precision for deferent languages such as English, French, German, Japanese and Korean. With respect to Korean, the isolation word recognition developed by ETRI (Electronics and Telecommunications Reach Institute) has been widely used.

Further, in another embodiment of the present invention, the responses from the examinee for the color function testing can not be allowed to be input into the computer system so that the examiner can modify the color function testing method. For example, when the examinee gives a response to a color-testing target, the examiner creates new color-testing targets to be used at the next test using the input device and such new color-testing targets may be made by changing the combination of red and green components.

In the preferred embodiments of the present invention, an additional preliminary examination may be carried out for roughly detecting the degree of examinee's visual acuity. For example, in the case where the examinee has the degree of 0.2, if the testing is made in a range of approximately 0.2 based on fact that he can not discriminate the degree of 0.1, the testing may be quickly and precisely achieved.

Accordingly, in the preliminary examination, several targets may be displayed in a picture simultaneously or one by one. The kinds of targets can be randomly produced, selected by the examiner, or selected by a predetermined order to be programmed.

In the case where the various degrees of targets are displayed in a picture at once, the smallest targets to be discriminated are evaluated through the examinee's response to one target or several targets.

Also, in the case where several targets may be displayed in a picture one by one, the targets are progressively displayed from the smaller ones to the larger ones and vice versa.

Therefore, during the examination procedures, the highest degree of the examination, which is discriminated by the examinee, is considered as his visual acuity or the decision of his visual acuity can be made after an additional examination to verify the evaluated visual acuity.

The preliminary examination to roughly detect the degree of the examinee's visual acuity is applied to the color function in such a manner as to be mentioned above. So, the detailed description of the color function testing will be described below.

In the present invention, if targets to be used in the visual function and responses to the targets are stored in a nonvolatile memory so that the data in the memory can be read out by serial numbers, names, identification numbers, and examinee's specific numbers, an oculist can confirm the variation of the patient by using the same targets in the next examination. The nonvolatile memory may be auxiliary memories such as a hard disk, floppy diskettes, optical magnetic disks or CD-ROMs.

This visual function testing according to the present invention is characterized in that an oculist exactly evaluates the condition of an ophthalmic ailment or a patient to be operated on his eye through the objective data and precise degree of the visual acuity.

In the conventional eye examination that has been used in schools, opticians and public health centers, the examinee is in need of an additional person indicating the targets.

However, in the automatic visual acuity testing according to the present invention, the targets are automatically produced on a screen by instructions of an examinee or an examiner, the computer system itself receives a number of responses to the different targets and decides the examinee's visual acuity, and the computer system outputs the results through an output device.

In similar, in the automatic color function testing of the present invention, the color-testing targets are automatically produced on a screen by instructions of an examinee or an examiner, the computer system itself receives a number of responses to the different color-testing targets and evaluates the examinee's color function, and the computer system outputs the results through an output device.

There may be a case where the examinee deceives his own visual function in order to gain the higher degree than actual degree he has and vice versa. This deceit may be achieved by memorizing the visual-testing and color-testing targets and order of such targets. It is possible for such an examinee to memorize the targets because the number of targets is small.

Accordingly, the conventional visual function testing doesn't prevent such an examinee from intentionally feigning his visual function.

The present inventions can reduce the probability of intentional feint of the examinee, which often occurs in the subjective visual function testing, and subjective errors. That is, such subjective errors are reduced by randomly producing the testing targets and checking the validity of the test result (e.g., whether there is any unreliable response to the testing targets).

For example, the computer system according to the present invention checks the validity of the result of examination before deciding the degree of the examinee's visual function, by randomly producing the size and shape of the targets, and changing the display order of the targets or the contrast of the targets If there is any suspicion of the validity of the results, the examination is repeated or the examination is declared invalid, thereby reducing errors, which are generated in the subjective examination, and making the result of the examination objective.

The color function testing according to the present invention also makes the result of the examination objective, thereby increasing the accuracy of the color function.

For example, various color-testing targets are randomly produced and it is ascertained whether there is any invalid result or not. Especially, in the case where a person, who has an abnormal color function, deceives his actual color function in order to obtain a normal decision in such a manner as to memorize color-testing targets in advance or in the case where a person, who has a normal color function, deceives his actual color function in order to obtain a color blindness decision in such a manner as to intentionally give wrong responses to color testing targets, the color function test according to the present invention can prevent such a deceit.

First, the color function testing according to the present invention ascertains whether there is any abnormality in the examinee's color function or not, and then inspects a kind of color blindness. Of course, the color blindness and the kind of it can be inspected by the conventional color-testing targets.

If the kind of color blindness is the red blindness, the red blindness standard is subdivided into several degrees by producing a plurality of the color-testing targets in which the red component is gradually increased in amount.

Next, the degree of the red blindness is evaluated using the amount of red component, which is included in the color-testing targets to be discriminated. At this time, such degrees of the red component may determine the precision of the red blindness.

On the other hand, the same color function testing as the red blindness may be applied to both a deuteranope and a tritanope.

The above-mentioned validity verification of visual function will be described below.

First, the concept of the validity verification and the effects thereof will be described.

The validity verification is to ascertain whether there is any unreliable result in the visual function testing. If the results of the visual function testing are interpreted as unreliable one, the results may be considered as invalid.

Accordingly, in the case where the results are considered as invalid, the visual function testing is carried out once more or the preciser testing is required to guarantee the validity of the testing. Of course, with respect to such invalid results, the final decision to declare the testing itself invalid can be issued.

The degree, which is used in the visual acuity, means a degree of eye strength determining the size of visual-testing target. The more the value of degree is increased, the more the eye strength is increased.

Although the degrees are the same, the size of visual-testing targets can be different from each other according to the kinds of visual-testing targets, which is uncommon. However, for the purpose of the explanation, it is assumed that the more the degree is increased, the smaller the size of the visual-testing target is. That is, the target size in the degree of 1.0 is smaller than that of 0.9.

Uncooperative examinees to intentionally deceive a response to the visual-testing target are classified into three groups, i.e., an upward group which wishes to obtain the higher degree of the visual function than his actual degree thereof, a down group which wish to obtain the lower degree of the visual function than his actual degree thereof, and an reckless group without any aim in mine.

The reckless group may be inspected easily with the above-mentioned validity verification. In this case, the results may be considered as invalid without further action. Accordingly, the present invention will be described with respect to the first two cases.

First, the upward group will be described below in detail.

The examinees in the upward group are persons who deceive responses to the visual-testing targets in order to obtain a normal decision in such a manner as to memorize visual-testing targets in advance.

If there is a possibility of the deceit that the examination result is higher than the degree of actual visual acuity, the present invention detects such a possibility and verdicts the examination as invalid.

To prevent this upward deceit of the examinee, the present invention includes the validity verification step to randomly produce the visual-testing targets in size and kind thereof.

Since it is impossible for the examinee to randomly memorize the produced targets in advance and the examinee gives the computer system (or examiner) right responses to only discernable targets, the deceit can not be achieved by his memory.

As a result, the visual acuity is tested only when the result is valid, thereby preventing the examinee from intentionally feigning his visual function.

The downward group will be described below in detail.

The examinees in the downward group are persons who deceive responses to the visual-testing targets in order to intentionally obtain the lower degree of his visual acuity.

If there is a possibility of the deceit that the examination result is lower than the degree of his actual visual acuity, the present invention also detects such a possibility and verdicts the examination as invalid.

The prevention of this downward deceit may further include various methods, which are not included in the prevention of the upward deceit. For example, new middle degrees of the discrimination targets, which are not in the conventional visual-testing targets, can be applied to that or the position of the visual-testing targets can be changed in order that it is impossible to compare relative sizes of the visual-testing targets. In addition, the small and large visual-testing targets are simultaneously displayed on a screen or the size and contrast of the visual-testing targets undergo a change. For the visual-testing targets to which wrong responses are issued, at least two examinations are carried out using the same visual-testing targets or other visual-testing targets in the same degree.

Although the visual function testing is explained for the visual acuity testing, the same methods may be applied to the color function testing.

The more detailed description for the validity of the visual function testing will be described below.

First, the visual acuity testing will be described before the color function testing.

In the visual acuity testing, if there are right and wrong responses to targets of the same degree and the same contrast, the validity of the testing may be doubtful. If there is a case that the examinee gives a right response to the testing targets although he gives a wrong response to the larger testing targets (in higher degree), the validity of the testing may be doubtful. Further, if there is a case that the examinee gives a wrong response to a target and he gives a right response to other targets in the same degree with low contrast, the validity of the testing may be also doubtful. When the examiner (or the computer system) enlarges the size of a target to which the examinee gave a wrong response but reduces the contrast to such a degree that the examinee, who had given the wrong response, can not discriminate the enlarged target, if he gives a right response to the enlarged target with the low contrast, the validity of the testing may be also doubtful. Although the contrast is reduced, if he gives a wrong response to a testing target enlarged to such a degree that the examinee, who had given a right response, can discriminate the enlarged target, the validity of the testing may be also doubtful.

The variation of the contrast may be carried out by various methods.

According to the present invention, the degrees of the contrast are made by controlling the background color, the color of target being maintained. For example, the background color of the target is varied from white color to black color with the progressive increase of the black component. That is, the amount of gray tone indicating darkness is used for the variation of background of the target.

On the other hand, the examinee can presume the discrimination of the target in the vicinity of the boundary between a degree capable of being discriminated and another degree capable of not being discriminated. Although the discrepant response is generated unintentionally, these may be a little difference in evaluating his visual function.

If such a discrepant response is repeatedly once, twice or several times, the present invention considers the testing invalid. Further, in the case where the difference between degrees of two targets, in which the discrepant responses are issued, is of the degree of 1 and within the predetermined degree, such an unintentional discrepancy can be disregarded as valid. For example, in the validity of the visual acuity testing according to the present invention, if the difference between two targets in size is less than a predetermined value, the validity is considered as valid.

On the other hand, in the case of color function testing, a number of color-testing targets, for example, targets discriminated by normal and abnormal persons, or targets which can not discriminated by a "protanope", a "deuteranope" or a "tritanope." are produced. Also, the color-testing targets for red are produced by varying the red component therein, which some or total red blindness persons can not discriminate. Also, with respect to the color-testing targets which are not discriminated by a "deuteranope" or a "tritanope," the color-testing targets are also produced by varying the their components therein.

In addition, it is ascertained whether there is any discrepancy in inspecting validity of the color function testing.

For example, in the case where an examinee gives wrong response to a color-testing target to which a normal person for color blindness and abnormal person can give right response, or in the case where they give both wrong response and right response for two color-testing targets which they are not able to discriminate or they must discriminate, the validity of the color function testing may be suspicious.

To be more particular, the above-mentioned validity is checked in the case where the examination is carried out for two different color-testing targets, which are produced in order that the combination of the color-testing target to be discriminated and background of it has the same discrimination degree. Also, if the examinee had already given a right response to a high degree color-testing target; but he gives a wrong response to a low degree color-testing target, the validity of the color function testing may be suspicious. That is, the color-testing targets, which may be easily discriminated with the increase of the red component, may be used for a protanope. In such a manner, the color-testing targets, which may be easily discriminated with the increase of the green component, may be used for a deuteranope. As mentioned above, if the examinee had already given a right response to a high degree color-testing target; but he gives a wrong response to a low degree color-testing target, the validity of the color function testing may be suspicious.

However, if one of red, green, blue components is varied too much, it is difficult for the normal person to discriminate the color-testing targets so that the increase and decrease of color should be made within a predetermined range. Further, with respect to the color-testing targets (normal person can discriminate) to which the examinee gives wrong responses, if one of red, green and blue components is decreased up to a range in which he can not discriminate it; nevertheless, he gives a right response to the such targets, the validity may be suspicious. As mentioned above, when such discrepancy responses are repeatedly issued several times, the examination is considered as invalid.

The above mentioned validity can be determined by additional conditions.

In the preferred embodiment of the present invention, the precision of the examination is achieved by providing the fine degrees of the visual-testing targets.

The visual-testing targets are elaborately produced within resolution of the computer system, by using outline information, which can be employed in varying the size of the targets. To produce these elaborate visual-testing targets, font data producing the outline are typically used. For example, the visual-testing targets are stored in the true type font and the outline is miniaturized or enlarged when they are displayed on a screen. Further, it is clear that other display methods can be used in miniaturizing or enlarging the characters or marks used in the visual acuity testing.

Accordingly, it is possible to take much closer testing by more subdividing the conventional visual-testing targets table, in which the degrees of them are limited ten and more, into tens of or hundreds of degrees.

In the conventional method, "Han's visual-testing targets" in which the visual acuity is decided by degrees of ten and more steps such as 1.0, 0.9, 0.8, etc. and "visual-testing targets of Yong-Han Jin" in which the size of target is classified by log-scaled degrees of fourteen and more steps were mainly used. However, since in such methods the tested visual acuity is decided by the conventional visual acuity degree, there is a problem that the visual acuity, which is not shown in the visual-testing targets, is decided by a degree which is substantially far from the exact visual acuity of the examinee.

However, according to the present invention, there is a merit that the visual acuity is decided by high accuracy such as 0.11, 0.12, 0.13, etc. because the visual-testing targets can be produced by any size allowed in the screen.

Further, according to this present invention, it is available to take prompt testing even in the case of examining many degrees of the targets to obtain the high accuracy, by applying a binary search to the visual acuity testing having many degrees of the targets. For example, in the case of the visual-testing targets subdivided by 64 degrees, even highest degrees of the targets can be obtained through the testing of about 6 or 7 targets.

In addition, in the present invention, apart from the conventional method, in which such size as in advance prepared in visual-testing targets is only examined, more exact testing can be carried out by finding out the smallest size target which the examinee can recognize, calculating the examinee's visual acuity from such a size, and by taking into account of the distance between the examinee and the screen.

In the meantime, at the time of color function testing in the visual function according to the desirable embodiments of the present invention, the state of color blindness can be decided by high accuracy similar to the visual acuity testing.

In the color function testing using the conventional color function table such as color-testing targets of "H-R-R" or "Cheon-Seok Han", the states of the color function states are divided to three degrees of "Serious", "Good", and "Weak". In contrast, according to the present invention, the sates of color function abnormality are precisely classified, by dividing color-testing targets which a protanope feels difficult in discriminating into many kinds of targets and testing many color-testing targets produced from variously changing red color component for each target. Further, as for the color-testing targets a deuteranope or a tritanope feels difficult, the states of color function abnormality is also precisely classified by testing many color-testing targets produced by converting each green and blue color components step by step.

To specifically examine, in the case of color-testing targets deciding red color abnormality divided into 10 steps (that is, color-testing targets for red color), such degrees as 1,2,3,4,5,6,7..., etc. are assigned according to the order of discrimination difficulty from easiest color-testing target to most difficult color-testing target, producing various degrees in the relative difficulty of discrimination for many other color-testing targets, and assigning the same degree for the color-testing targets having the same difficulty of discrimination.

As described above, the subdividing method of color-testing targets explained in the color-testing targets for red color is equally applied to both the color-testing targets for green and blue colors.

According to the present invention, other precise tests are carried out, as similar method as visual acuity testing, by producing the graded color-testing targets as above.

The color function table being graded as above, the degree of color-testing targets is considered as that corresponding to the visual acuity degree and the kinds of color-testing targets are considered as those of visual-testing targets. The degree of color-testing targets is theoretically subdivided up to about 255 steps in the case of visual function testing device (i.e., the computer system) in which red, green and blue are expressed by 8 bit and, in the case of using more bit for the expression of pixel, more precise degrees are available. Additionally, in the case of color function testing, the abnormality is decided by the subdivided value, by even only small number of testing, and by the binary search.

Figure 3:
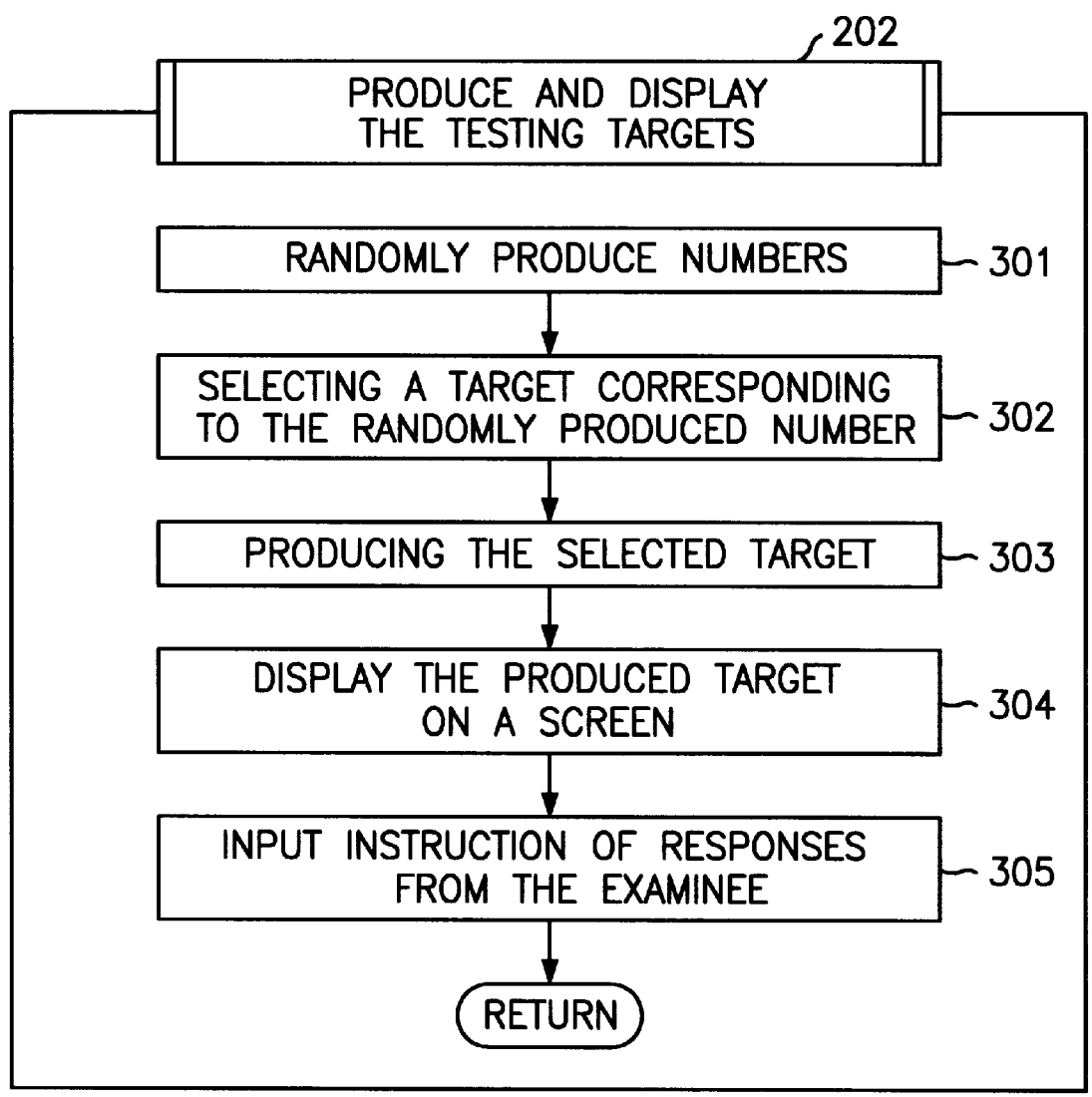
FIG. 3 is a detailed flow chart for producing and marking visual-testing targets according to the present invention.

FIG. 3 is a detailed flow chart for producing and marking visual-testing targets according to the present invention.

First of all, visual-testing target to be marked on the screen are randomly selected at steps 301, and 302.

The selected visual-testing target is sampled at step 303 and marked on the screen at step 304.

If the visual-testing target is marked on the screen, the examinee is heard of the explanation of input method or output messages such as indicating an input order at step 305. At this point, sound or voice message being transmitted through speaker is used and it is also available to use a special output device, additionally equipped for giving the screen or the examinee instructions.

The visual acuity testing device may store testing procedures therein and decide a target to be displayed next according to the visual-testing response collected up to the present or according to randomly samples randomly produced. In this embodiment, a random number is first sampled at step 301 in order to select visual-testing target and then the visual-testing target corresponding to the sampled number is decided. At this point, randomly sampling of the visual-testing target is for increasing the confidence of validity testing.

The progress to randomly sample the visual-testing target at step 301 has various methods: mapping time stamp of click existing inside of computer onto a numeral within a certain range; sampling the random number and deciding the visual-testing target by using the remnant, which is obtained from dividing such a number by the number of target available for sampling, as an index.

Since the generation of the random number is well known, it will not be explained there.

FIG. 4 is a detailed flow chart in connection with a method for inputting visual-testing response according to the present invention.

First of all, the examinee's visual-testing response is inputted into a mike by activating the mike at step 401 in order for the voice to be inputted at step 402.

And then, the visual function testing device senses the inputted response by carrying out the sensing of the voice at step 403 and transmits the sensed response as a visual-testing response at step 404.

FIG. 5 is a detailed flow chart for checking the visual-testing responses according to the present invention.

First of all, the precision for the visual-testing responses is decided first at step 501.

Further, the responses to the visual-testing targets are recorded at step 502. At this point, it is available for saving data in database or file as well as recording the responses to the visual-testing targets.

For example, in the case of visual acuity testing, it is decided first whether the responses are accorded with the targets. In the case of color function testing, it is decided whether the responses are sensed to a protanope, a deuteranope, a tritanope or normal person, or are accorded with the visual-testing target.

Figure 6A:
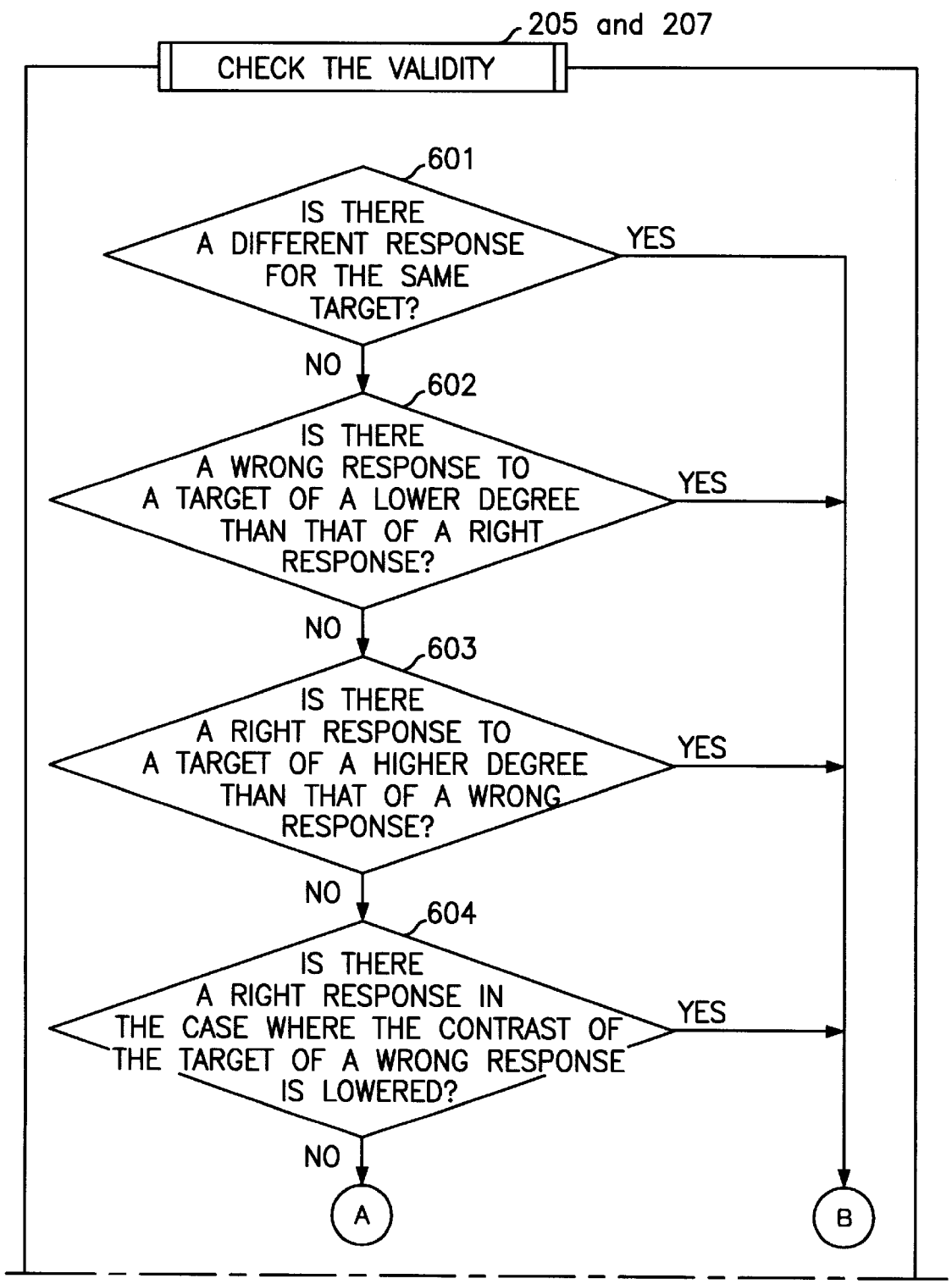
FIG. 6 is a detailed flow chart for validity testing according to this invention.
Figure 6B:
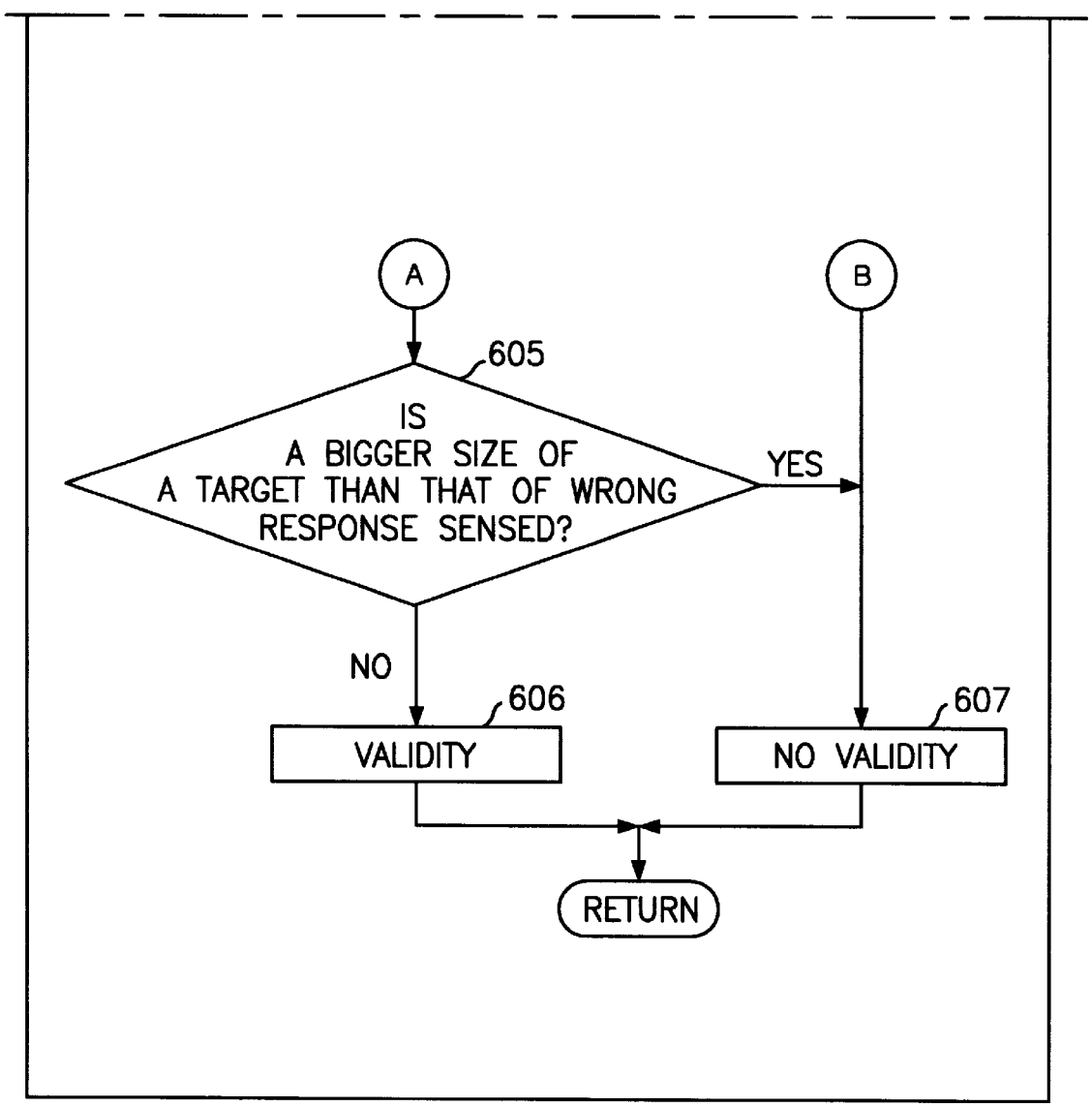

FIG. 6 is a detailed flow chart for the validity testing according to the present invention.

If a different response exists for the same target at step 601, it is considered that there is no validity at step 607.

Further, at step 602, if there is a wrong response to a target of a lower visual acuity degree than that of right response, it is considered that there is no validity at step 607.

Further, at step 603, if there is a right response to a target of a higher visual acuity degree than that of a wrong response, it is considered that there is no validity at step 607.

If there is a right response in the case where the contrast of the target of a wrong response is lowered at step 604, it is considered there is no validity at step 607.

In the case where a bigger size of a target than that of a wrong response is sensed in a certainly low contrast at step 605, it is considered there is no validity at step 607.

If there is no case conforming to any case mentioned as above, it is considered that there is validity at step 606. It may be possible to constitute the validity conformation so as to sense the invalidity only when the number of discrepancy cases as above is more than a certain frequency.

Figure 7A:
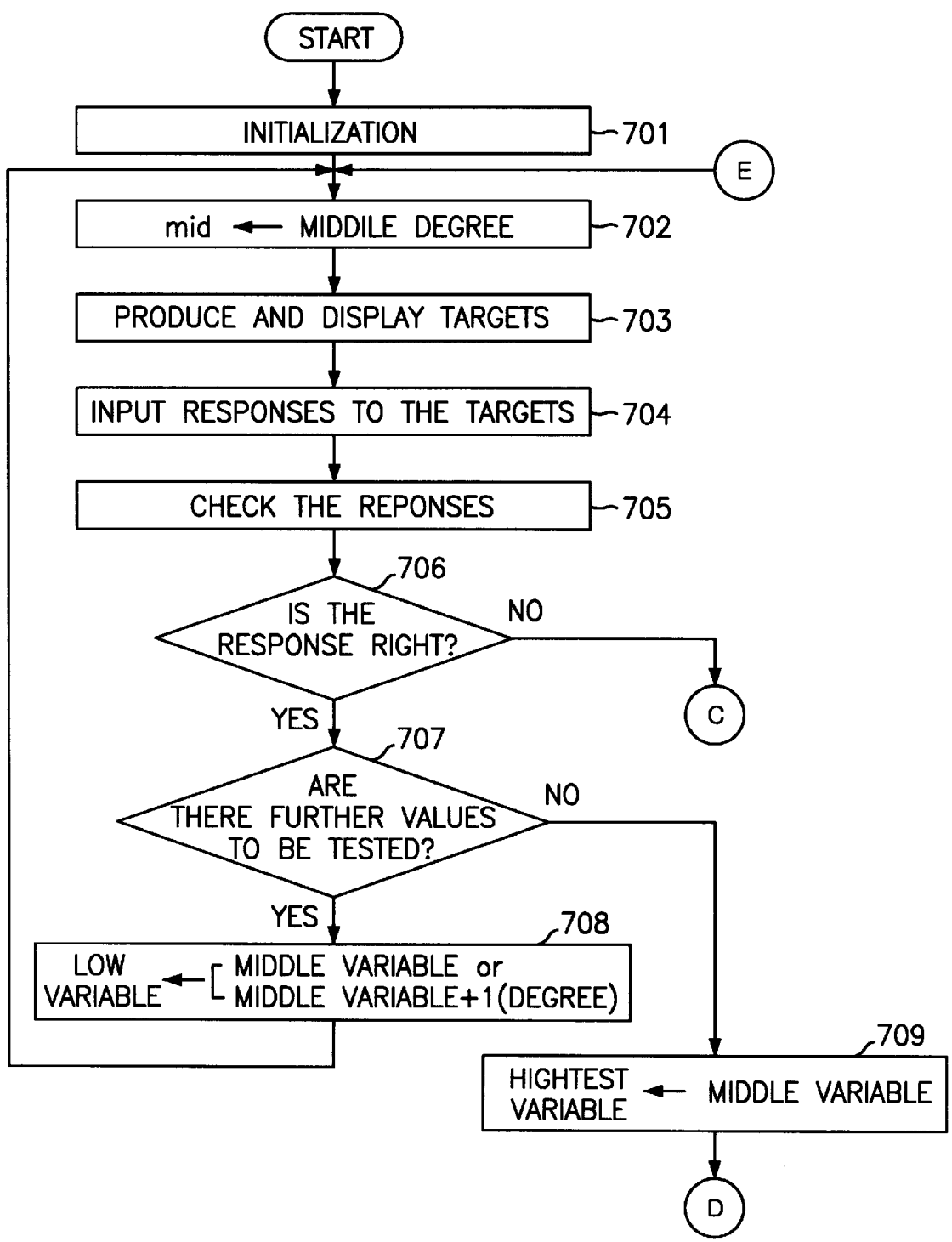
FIG. 7 is a flow chart illustrating a binary search of the visual function testing according to this invention.
Figure 7B:
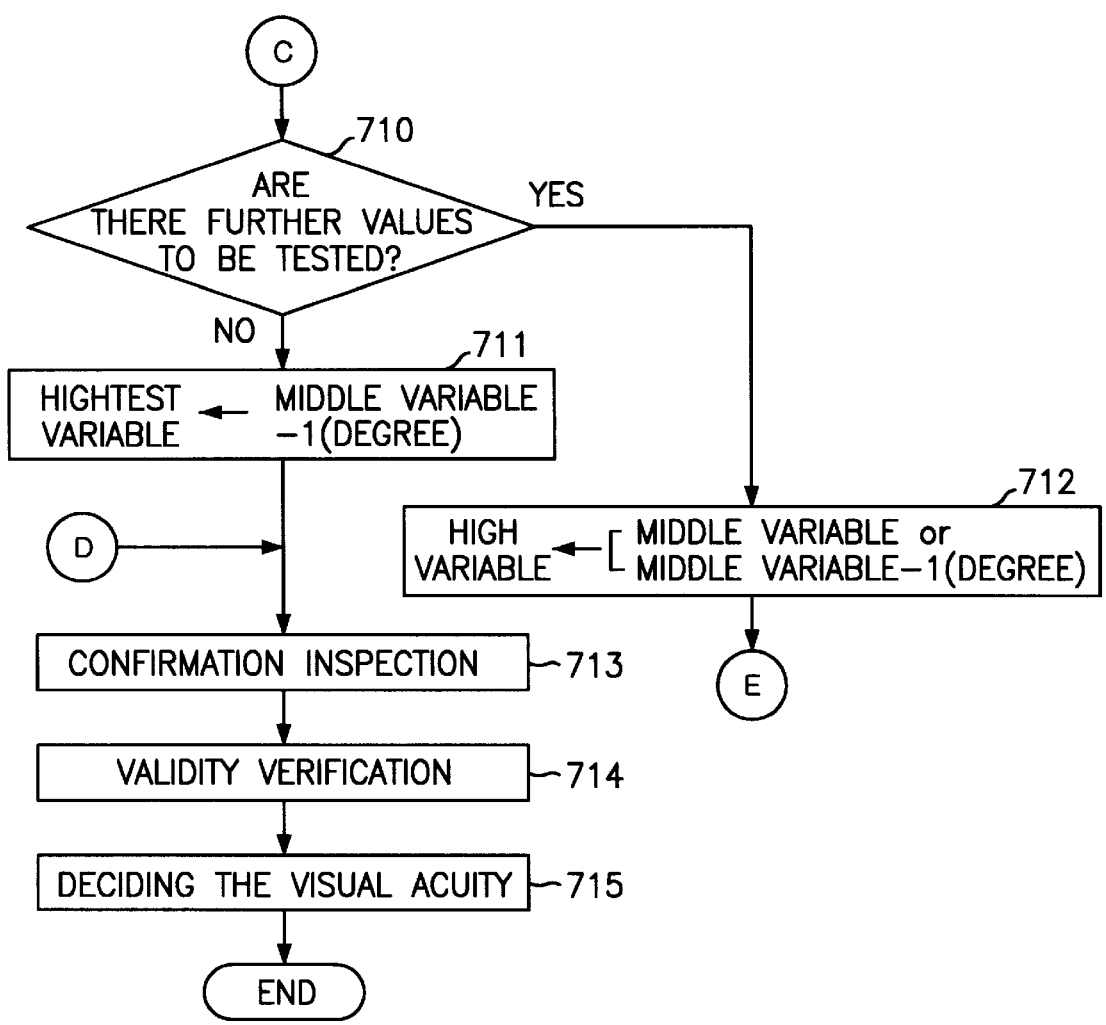

FIG. 7 is a flow chart for visual function testing according to the present invention.

In the visual function testing according to another embodiment of the present invention, the more difficult to sense, the more increased value the visual-testing target is assigned as a degree, according to the relative difficulty. For example, in the case of visual acuity testing, a target to be discriminated to test is assigned in order of increase from low degrees to high degrees.

In the visual acuity testing according to another embodiment of the present invention, it is available to variously change the size of targets marked on the screen, by expressing the targets by outline information, and to sample much rather subdivided targets of visual acuity degree than the conventional visual acuity target such as 0.05, 0.10, 0.15, 0.20 . . . 1.80, 1.90.

In order to promptly test precise visual function by many target minutely divided, visual function testing applying binary search for degrees to be included in the testing range is carried out.

The binary search used in this testing is different from common one. That is, the target to search is not in advance decided and it is possible to take a search even though values included in testing range are not in advance saved in array or list.

Accordingly, it is obvious that it is possible to obtain the same effect as this embodiment although binary search is carried out after saving the searched values in array or list.

In the meantime, as for color-testing targets for red, green and blue, it is possible to promptly test the abnormality of color function by applying the prior search, as the visual acuity testing, assigning the value to let the visual-testing targets have an order according to the relative difficulty.

The visual acuity testing implemented in the computer system will be described in detail. Also, the color function testing using color-testing targets subdivided in degree may be implemented by the above-mentioned method.

First, an initialization is carried out at step 701.

For example, at the initialization step (step 701), intervals between degrees in the testing range and neighboring degrees are determined and a low variable having the lowest value (lower limited value) and the high variable having a highest value (upper limited value) are initialized. At this time, at least one degree (a value corresponding to the target), that the examinee can discriminate, must be included in the testing range.

Next, when the values included in the testing range are arranged, a middle variable is changed into a middle value of the middle degree between the lowest value and the highest value in the search range at step 702.

Subsequently, a visual-testing target of a degree corresponding to the middle variable is displayed on a screen at step 703. Step 202 producing the visual-testing targets in FIG. 3 may be an example of step 703.

Responses to the displayed targets are inputted into the computer system of the present invention at step 704 and the input responses are checked at step 705, that is, it is ascertained whether the input responses are right or wrong at step 706.

If the responses are right, it is determined whether there exist further targets to be tested in the testing range at step 707.

If there is no visual-testing target in the testing range, this middle variable is considered as the highest discrimination degree (i.e., highest variable) of the examinee at step 709 and the final visual acuity is evaluated at step 715. At this time, the highest variable is a variable to store a value corresponding to the highest degree the examinee can discriminate.

If it is required to examine further visual-testing targets in the testing range, new lower variable is changed into the middle variable (or the middle variable +1 degree) at step 708 so that only the right values of the middle variable (further higher degree) are examined and a new middle variable is changed into a middle value in the modified range at step 702.

In the result of the visual acuity testing in such a new range, if a wrong response is issued, it is determined whether it is required to examine further visual-testing targets in such a testing range at step 710.

If there is no visual-testing target to be examined in the testing range, the testing range is divided in two and, of values in the testing range, the left value (i.e., just low degree) of the middle variable is considered as the highest discrimination degree of the testing at step 711 and the final visual acuity is evaluated at step 715.

In similar, if it is required to examine further visual-testing targets in the testing range, the testing range is divided in two and the middle variable (or the middle variable −1 degree) is changed into a new high value at step 712 in order that the left values of the middle variable are examined. When the values within the modified testing range are, in this order, arranged, the middle variable is set to a middle value of the arranged values at step 702.

If necessary, the visual acuity further comprises an additional step (step 713) in which neighboring values of the testing range are examined for more precise testing or the validity verification step (step 714).

Accordingly, in the case where the validity verification step is carried out, the additional examination (step 713) and the validity verification (step 714) may be carried out before the evaluation of the final visual acuity (step 715).

As mentioned above, the visual function testing according to another embodiment of the present invention improves the precision of the testing, by using more subdivided targets and providing a value for each target so as to compare an order of them. Further, fast and precise testing is achieved with the binary search.

The production and grading of the testing targets are described above.

The binary search, which is described above, can use the recursion instead of the loop and also pointer operation instead of the index. This modification has the same effect of the above-mentioned embodiment and, therefore, can be implemented by the same embodiment.

The procedures of step 706 checking whether the responses are right or wrong and steps 707 and 710 determining whether there is further targets to be tested in the testing range can be changed with the same effect.

Steps 708, 709, 711 and 712 changing the low and high values in the testing range can be carried out before steps 707 and 710 which ascertain whether there is further targets to be tested in the testing range.

Furthermore, step 705 checking the responses, which is carried out separately, can be included in step 706 ascertaining whether the input responses are right or wrong.

The steps illustrated in attached figures can be changed or modified in the same effects mentioned above and the possibility of this change and modification will be apparent to those skilled in the art.

In the preferred embodiment, the resources required to implement the computer system for visual acuity may be saved, by performing the search without storing the targets to be searched in a memory. Further, since the present invention arranges and stores the search values in the testing range in advance in carrying out the binary search, the search can be carried out in the reduced range whenever the search range is repeated.

Although the values in the testing range don't have a uniform interval, the values are be stored in an arrangement or a list and the binary search whose range is reduced to a half can be carried out whenever the search range is repeated.

The embodiment of the present invention is described, as the values become higher with the increase of the degree of difficulty, however, the values become lower with the increase of the degree of difficulty.

In another embodiment of the present invention, the values of targets to be tested can be stored in descending order in a memory.

In the response input, the examinee doesn't input the discrimination value into the computer system but the examiner can input the responses from the examinee into it after ascertaining whether the responses are right or wrong.

While the present invention has been shown and described with reference to the particular embodiments, it will be apparent to those skilled in the art that many changes and modifications may be made without departing from the spirit and scope of the invention as defined in the appended claims.

As apparent from the above description, the present invention improves subjective errors caused by the subjective visual function testing and may be easily used in a visual function testing requiring an objective and exact testing results in such as military affairs, vocational aptitude test, driving license, insurance against loss, observation of an ophthalmic ailment. Further, automatic testing method of the present invention is widely used in hospitals, opticians, schools, companies, public health centers, other organization and households where it is difficult to take professional advice with a low cost.

What is claimed is:

1. A method for testing a visual acuity and color function of an examinee using a computer system, comprising the steps of:
    a) selecting at least one target to be discriminated;
    b) producing the at least one target on a screen of the computer system;
    c) inputting a response to the at least one target from the examinee;
    d) ascertaining whether the response is right or wrong so as to evaluate a validity of the response;
    e) repeatedly carrying out the steps (a) to (d) with other targets selected in said selecting step, according to the validity of the response;
    f) comparing responses to the at least one target and the other targets and evaluating a validity of the visual acuity and color function; and
    g) deciding the visual acuity and color function of the examinee based on the validity evaluated in the comparing step.

2. The method in accordance with claim 1, wherein the step of f) considers the validity as invalid when different responses to the same targets are given from the examinee.

3. The method in accordance with claim 1, wherein the step of f) considers the validity as invalid when the examinee gives a right response to a smaller target than that to which he gives a wrong response.

4. The method in accordance with claim 1, wherein the step of f) considers the validity as invalid when the examinee gives discrepant responses to the same targets several times.

5. The method in accordance with claim 1, wherein the step of f) comprises the step of testing the visual function using the targets having different contrast.

6. The method in accordance with claim 1, wherein the step of f) considers the validity as invalid when the examinee gives a right responses to a target of low contrast although he gives a wrong response to the same target.

7. The method in accordance with claim 1, wherein the step of f) considers the validity as being invalid when the computer system enlarges a size of a predetermined target to which the examinee gave a wrong response but reduces a contrast of the predetermined target to such a degree that the examinee can not discriminate the predetermined target after being enlarged, if the examinee gives a right response to the enlarged target with the low contrast.

8. The method in accordance with claim 1, wherein the step of f) considers the validity as invalid when the examinee gives a wrong response to a low contrast target but enlarged to such a degree that he, who had given a right response, can discriminate the enlarged target.

9. The method in accordance with claim 1, wherein the step of f) comprises the steps of:
    g) ascertaining whether there is a discrepant response to the same targets;
    h) ascertaining whether there is a wrong response to a lower degree target than that to which the examinee gave a right response;
    i) ascertaining whether there is a right response to a higher degree target than that to which the examinee gave a wrong response;
    j) ascertaining whether there is a right response to a higher degree target and the same degree target to which the examinee gave a right response;

k) when the computer system enlarges a size of a target to which the examinee gave a wrong response but reduces its contrast to such a degree that the examinee, who had given the wrong response, can not discriminate the enlarged target, ascertaining whether there is a right response to the enlarged target; and l) considering the validity as invalid, if there exist such cases as many as the predetermined number of times.

10. The method in accordance with claim 1, wherein the step of a) randomly selects one from available targets.

11. The method in accordance with claim 1, wherein the step of b) produces at least two targets on the screen.

12. The method in accordance with claim 1, wherein the step of c) further comprises the step of inputting an accuracy of the response from the examinee.

13. The method in accordance with claim 1, wherein the step of d) further comprises the step of storing the targets and the response from the examinee in an auxiliary memory.

14. The method in accordance with claim 1, wherein the target is true type font data whose size is variable.

15. The method in accordance with claim 1, wherein the target is color-testing target for a color function testing.

16. The method in accordance with claim 15, wherein the method further comprises the step of changing a red component of the color-testing target.

17. The method in accordance with claim 15, wherein the step of b) produces at least one color-testing target which a protanope and a deuteranope discriminate differently.

18. The method in accordance with claim 15, wherein the step of b) target produces at least one pair of targets which have the same color components, except for a red component.

19. The method in accordance with claim 15, wherein the step of b) target produces at least one pair of targets which have the same color components, except for a green component.

20. The method in accordance with claim 15, wherein the step of f) considers the validity as invalid when the examinee gives different responses to at least one pair of targets which have a different amount of a red component.

21. The method in accordance with claim 15, wherein the step of f) considers the validity as invalid when the examinee gives different responses to at least one pair of targets which have a different amount of a green component.

22. The method in accordance with claim 15, wherein the step of f) considers the validity as invalid when the examinee gives a wrong response to a target which is discriminated by a normal person and a protanope.

23. The method in accordance with claim 15, wherein the step of f) considers the validity as invalid when the examinee gives different responses to a target which is discriminated by a protanope.

24. The method in accordance with claim 15, wherein the step of f) considers the validity as invalid when the examinee gives different responses to a target which is not discriminated by a protanope.

25. The method in accordance with claim 15, wherein the step of f) considers the validity as invalid when the examinee gives different responses to a target which is discriminated by a deuteranope.

26. The method in accordance with claim 15, wherein the step of f) considers the validity as invalid when the examinee gives a response corresponding to a protanope or a deuteranope to a target which is differently discriminated by a normal person, a protanope and a deuteranope.

27. A method for testing a color function of an examinee using a computer system, the method comprising the steps of:

i) displaying at least one color-testing target which is differently discriminated by a normal person and protanope;

ii) deciding the examinee to be a protanope if the examinee gives a response to the target, which is discriminated by a protanope; and iii) checking a degree of red blindness by using at least two targets having a different amount of a red component.

28. The method in accordance with claim 27, wherein the step of iii) checks a degree of red blindness based on the highest degree of the targets which the examinee discriminates.

29. The method in accordance with claim 27, wherein the step of iii) uses a pair of targets having the same color components except for the red component.

30. The method in accordance with claim 27, wherein the step of iii) checks a degree of red blindness based on the smallest amount of red component included in the targets which the examinee discriminate.

31. A method for testing a visual function of an examinee using a computer system, the method comprising the steps of:

1) displaying on a screen a middle value target in a testing range from a lower limited value to a upper limited value;

2) inputting a response to the middle value target from the examinee;

3) ascertaining whether the response is right or wrong; and 4) deciding the examinee's visual acuity, comprising the steps of:

4-1) if the response is wrong, changing the upper limited value based on the middle value target and repeatedly carrying out the steps of 1) to 3); and 4-2) if the response is right, changing the lower limited value based on the middle value target and repeatedly carrying out the steps of 1) to 3).

32. The method in accordance with claim 31, wherein the step of 4-1) changes a value just below the middle value target into a new upper limited value and wherein the step of 4-2) changes a value just above the middle value target into a new lower limited value.

33. The method in accordance with claim 31, wherein the visual function has visual-testing targets for a visual acuity and color-testing targets for a color-testing targets.

* * * * *